(12) United States Patent
Yamamoto et al.

(10) Patent No.: US 8,722,342 B2
(45) Date of Patent: May 13, 2014

(54) METHOD FOR ENHANCING SENSITIVITY OR METHOD FOR AVOIDING INFLUENCE OF HEMOGLOBIN IN IMMUNOLOGICAL MEASUREMENT

(75) Inventors: Mitsuaki Yamamoto, Ryugasaki (JP); Akiko Suzuki, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 310 days.

(21) Appl. No.: 13/002,467

(22) PCT Filed: Jul. 3, 2009

(86) PCT No.: PCT/JP2009/003097
§ 371 (c)(1),
(2), (4) Date: Jan. 3, 2011

(87) PCT Pub. No.: WO2010/001619
PCT Pub. Date: Jan. 7, 2010

(65) Prior Publication Data
US 2011/0104825 A1    May 5, 2011

(30) Foreign Application Priority Data

Jul. 4, 2008  (JP) .................................. 2008-175816
Jul. 4, 2008  (JP) .................................. 2008-175817

(51) Int. Cl.
*G01N 33/53*     (2006.01)

(52) U.S. Cl.
CPC ...................................... *G01N 33/53* (2013.01)
USPC ......... 435/7.1; 435/7.92; 435/7.93; 435/7.94; 436/518

(58) Field of Classification Search
None
See application file for complete search history.

(56) References Cited

U.S. PATENT DOCUMENTS

| | | | |
|---|---|---|---|
| 4,886,744 A * | 12/1989 | Arnost et al. ................ | 435/6.16 |
| 6,200,773 B1 | 3/2001 | Ouyang et al. | |
| 2008/0261328 A1 * | 10/2008 | Tanaka .......................... | 436/525 |

FOREIGN PATENT DOCUMENTS

| | | | |
|---|---|---|---|
| CN | 101119958 A | 2/2008 | |
| CN | 101160317 A | 4/2008 | |
| JP | 58 047256 | 3/1983 | |
| JP | 59 220646 | 12/1984 | |
| JP | 60 168 050 | 8/1985 | |
| JP | 10 90271 | 4/1998 | |
| JP | 2000 329764 | 11/2000 | |
| JP | 2007-114129 A | 5/2007 | |
| WO | WO 91/05605 | * 5/1991 | ............... B01J 13/02 |

OTHER PUBLICATIONS

Christensen et al., The Synthesis and Ion Binding of Synthetic Multidentate Macrocyclic Compound, Chem Rev. 1974, vol. 74, pp. 351-384.*
Kolthoff., Application of Macrocyclic Compounds in Chemical Analysis, Analytical Chemistry, vol. 51, No. 5, Apr. 1979, pp. 1-22R.*
Extended European Search Report issued on Mar. 1, 2012 in the corresponding European Patent Application No. 09773197.0.
Sang Wook Oh, et al.; Calixarene derivative as a tool for highly sensitive detection and oriented immobilization of proteins in a microarray format through noncovalent molecular interaction; The FASEB Journal express article 10.1096/fj.04-2098fje; vol. 19, No. 10, XP002669033, ISSN: 0892-6638, Jun. 6, 2005; pp. 1-21.
Combined Office Action and Search Report issued Sep. 10, 2013 in Chinese Patent Application No. 200980125714.2 with English translation of categories of cited documents, English only.
Sang Wook Oh, et al., "Calixarene derivative as a tool for highly sensitive detection and oriented immobilization of proteins in a microarray format through noncovalent molecular interaction", The FASEB Journal, vol. 19, No. 8, Jun. 6, 2005, pp. 1335-1337.
Zheng Xie, et al., "Synthesis and Properties of Oligo (arylenealkyne) Macrocycles", Chinese Journal of Organic Chemistry, vol. 22, No. 8, Aug. 31, 2002, pp. 543-554 with English abstract, with English portions only.
Ze-Li Yuan, et al., "Synthesis of New Schiff Base Macrocyclic Compunds", Chinese Journal of Organic Chemistry, vol. 26, No. 11, Nov. 30, 2006, pp. 1590-1593 with English abstract, English portion only.

* cited by examiner

*Primary Examiner* — Gary W Counts
(74) *Attorney, Agent, or Firm* — Oblon, Spivak, McClelland, Maier & Neustadt, L.L.P.

(57) ABSTRACT

A method for enhancing measurement sensitivity or avoiding hemoglobin influence in a latex agglutination or metal agglutination immunoassay method of a target antigen in a biological sample that uses calixarene in the immunoassay.

8 Claims, No Drawings

METHOD FOR ENHANCING SENSITIVITY OR METHOD FOR AVOIDING INFLUENCE OF HEMOGLOBIN IN IMMUNOLOGICAL MEASUREMENT

CROSS-REFERENCE TO RELATED APPLICATIONS

This application is a US National Stage Application of PCT/JP2009/003097, filed on Jul. 3, 2009, the text of which is incorporated by reference, and claims priority to Japanese Patent Applications 2008-175816 and 2008-175817, both filed on Jul. 4, 2008, the text of which is also incorporated by reference.

TECHNICAL FIELD

The present invention relates to a method for enhancing sensitivity or a method for avoiding the influence of hemoglobin in immunoassay, and to a reagent for use in the immunoassay.

BACKGROUND ART

In recent years, a variety of assay methods based on immunological reaction have been employed for assaying microlevel substances in samples. Such a variety of immunoassay methods include the RIA method, the EIA method, immunoturbidimetry, the latex agglutination method, the metal colloid agglutination method, and immunochromatography. Among them, the latex agglutination method, the metal colloid agglutination method, and the like are generally employed, since these methods require no separation or washing of reaction mixtures, which is advantageous for automated assay. In immunoassay, it is general that a suitable method according to the target substance concentration of the biological sample is selected. The latex agglutination method and the metal colloid agglutination enable more accurate determination of a substance in a microamount as compared with immunoturbidimetry, but the substance in a microamount cannot attain a microlevel assay that can be determined by the RIA method and the EIA method. In any of these immunoassay methods, there is demand for reduction in the scale of reaction system and shortening of measurement time, and enhancement in measurement sensitivity is an important issue.

One known technique for enhancing measurement sensitivity is addition of polyethylene glycol or a water-soluble polysaccharide such as dextran to the reaction system (Patent Documents 1 and 2). However, since these additives have a molecular weight distribution and are not a single compound, stable sensitivity-enhancing effect cannot be attained, which is one problem.

In any immunoassay method, non-specific reaction with various miscellaneous substances contained in a sample other than the target antigen-antibody reaction causes aggregation or absorption, which problematically results in a decrease in measurement precision. Particularly when a plasma-derived biological sample containing hemoglobin originating from hematocytes is assayed, hemoglobin may influence obtaining accurate measurements of immunoassay. Since the extent of hemolysis varies depending on sample, accurate measurements cannot be obtained. Thus, the influence of hemoglobin must be avoided by a certain technique.

Hitherto, there has been proposed a method for avoiding the influence of hemoglobin through addition of a surfactant to the reaction system (Patent Document 3). However, addition of a surfactant decreases measurement sensitivity in immunoassay, thereby failing to determine a target substance at high precision, which is problematic.

Patent Document 4 discloses an immunoassay method for CRP in a human serum sample by use of anti-human CRP rabbit serum, in which non-specific reactions which would otherwise be caused by a complement component can be prevented by adding a polyhydric phenol to the assay system. In one disclosed specific procedure, non-specific reaction which would otherwise be caused by a complement or the like can be successfully prevented by addition of sulfuric acid calix(6)arene in an amount of 5 mM. However, Patent Document 4 merely discloses the action of calixarene on the influence of complements in CRP assay of a human serum sample by use of anti-human CRP rabbit serum, and does not disclose how calixarene gives an effect on the measurement sensitivity or on the influence of hemoglobin. In addition, Patent Document 4 is silent on a method for assaying target antigen or antibody by use of an insoluble carrier (e.g., latex particles) sensitized with an antibody to the target antigen or an antigen to the target antibody.

PRIOR ART DOCUMENT

Patent Documents

Patent Document 1: JP-A-Sho 58-047256
Patent Document 2: JP-A-Sho 59-220646
Patent Document 3: JP-A-Sho 60-168050
Patent Document 4: JP-A-2000-329764

SUMMARY OF THE INVENTION

Problems to be Solved by the Invention

An object of the present invention is to provide a method for enhancing the measurement sensitivity of an assay target in an immunoassay, and a reagent for use in an immunoassay, which reagent realizes enhanced measurement sensitivity.

Another object of the present invention is to provide a method for avoiding the influence of hemoglobin (hereinafter referred to as hemoglobin influence avoiding method) in an assay system in which a target substance present in a biological sample such as a plasma sample is assayed through an immunoassay method.

Means for Solving the Problems

The present inventors have conducted extensive studies on the method for enhancing measurement sensitivity in immunoreaction. Quite surprisingly, the inventors have found that when a macrocyclic compound such as a calixarene is added to a reaction system at a low final concentration of 0.005 to 4 mM, the measurement sensitivity of the system can be enhanced, and therefore, a sample containing an assay target substance at a low concentration can be accurately assayed. Note that when the final macrocyclic compound concentration of the reaction system is 5 mM, an abnormal blank value is obtained, and enhancement in measurement sensitivity is no longer observed in response to an increase in the assay target substance concentration. The inventors have also found that when a macrocyclic compound is added to a reaction system containing an assay sample, the influence of hemoglobin contained in the assay sample can be avoided, thereby allowing accurate assay even a sample having a low assay target substance concentration.

Accordingly, the present invention provides a method for enhancing measurement sensitivity or a hemoglobin influence avoiding method in an immunoassay method, characterized in that the method comprises assaying target substance contained in a biological sample through antigen-antibody reaction in the presence of a macrocyclic compound.

The present invention also provides an immunoassay reagent for use in an immunoassay method in which an assay target substance contained in a sample is determined through antigen-antibody reaction, characterized in that the reagent comprises a macrocyclic compound as a main ingredient which acts as a measurement sensitivity enhancing agent or a hemoglobin influence avoiding agent.

Effects of the Invention

According to the method of the present invention, the measurement sensitivity of an assay target substance can be enhanced, whereby even a sample having a low assay target substance concentration can be assayed accurately. According to the immunoassay method of the present invention, the influence of hemoglobin present in a biological sample can be avoided. Thus, even when the sample contains hemoglobin, the sample can be assayed accurately. Furthermore, since the aforementioned macrocyclic compound (e.g., calixarene or cyclodextrin) is available as a single compound, stable effect of enhancing measurement accuracy can be attained without a lot-to-lot variation.

MODES FOR CARRYING OUT THE INVENTION

The sample employed in the method of the present invention is preferably a biological sample. Particularly, a biological sample which may contain hematocytes or hemoglobin originating from hematocytes is preferably employed. Examples of the biological sample include cerebrospinal fluid, tear, tissue fluid, blood, plasma, and serum. Of these, blood-derived samples; i.e., blood, plasma, and serum are particularly useful, since these samples often contain hemoglobin.

In the present invention, no particular limitation is imposed on the immunoassay method, so long as the method employs an antigen-antibody reaction between an assay target substance and a substance which undergoes antigen-antibody reaction with the assay target substance. Examples of the immunoassay method include immunodiffusion (SRID method), immunoturbidimetry, the hematocyte agglutination method, the latex agglutination method, the metal colloid agglutination method, the RIA method, and the EIA method. Among them, the latex agglutination method and the metal colloid agglutination method are preferred, since these methods provide high measurement sensitivity and are suited for automated analysis such as application to generally employed automated analyzers. Particularly, an immunoassay method employing an insoluble carrier sensitized with an antibody is more preferred.

Examples of the insoluble carrier include organic polymer particles, inorganic particles, and hematocytes. Examples of the organic polymer particles include those of insoluble agarose, cellulose, and insoluble dextran, and latex particles are preferred. Examples of the latex particles include those of polystyrene, styrene-methacrylic acid copolymer, styrene-glycidyl(meth)acrylate copolymer, styrene-styrenesulfonic acid salt copolymer, methacrylic acid polymer, acrylic acid polymer, acrylonitrile-butadiene-styrene copolymer, vinyl chloride-acrylic acid ester copolymer, and polyvinyl acetate-acrylate. If required, various modified latexes (e.g., carboxylic acid-modified latex) may be used. The mean particle size of the latex particles employed is appropriately 0.05 to 0.50 μm, depending on the type of analyzer and other factors. Examples of the inorganic substance particles include those of silica and alumina.

No particular limitation is imposed on the assay target substance in the method of the present invention, so long as the substance can be determined through an immunoassay method, and a variety of substance may be employed. Examples of the assay target substance an antigen, a hapten, an antibody, a hormone, and a drug. Among them, an antigen is preferably as an assay target substance, with a protein antigen being more preferred. Specific examples include CRP, fibrin and fibrinogen degradation products, D dimer, soluble fibrin (SF), lipoprotein (a) (Lp(a)), matrix metalloprotease-3 (MMP-3), prostate-specific antigen (PSA), IgG, IgA, IgM, IgE, IgD, anti-streptolysin O, rheumatoid factors, transferrin, haptoglobin, α1-antitrypsin, α1-acid glycoprotein, α2-macroglobulin, hemopexin, antithrombin-III, α-fetoprotein, CEA (carcinoembryonic antigen), ferritin, HBs-Ag (B-type hepatitis surface antigen), Anti-HBs (anti-B-type hepatitis surface antibody), HBe—Ag (B-type hepatitis e-antigen), Anti-HBe (anti-B-type hepatitis e-antibody), and Anti-HBc (anti-B-type hepatitis core antibody). Of these, CRP, fibrin and fibrinogen degradation products, D dimer, SF, Lp(a), MMP-3, PSA, etc. are preferred. Needless to say, the assay target substance is not limited to the above substances.

The substance which undergoes antigen-antibody reaction with the aforementioned assay target substances (hereinafter referred to as immunoreactive substance) is an antibody for the assay target substance, when the assay target substance is an antigen, hapten, etc. When the assay target substance is an antibody, a corresponding antigen is used. The antigen and antibody serving as an immunoreactive substance may be prepared through a conventional method. The antibody may be a polyclonal antibody or a monoclonal antibody, or an Fab fraction, an $F(ab')_2$ fraction, etc.

The macrocyclic compound employed in the present invention is a functional molecule that allows metal ions, an inorganic substance, an organic substance, etc. to be taken into pores of the molecule. No particular limitation is imposed on the macrocyclic compound, and a variety of such compounds may be used. Examples of the macrocyclic compound include calixarenes, cyclodextrin, and crown ether. Derivatives and modified forms thereof may also be used. Among them, macrocyclic compounds having pores that readily include a hydrophobic molecule and at least four hydrophilic functional groups are preferred. Examples of the hydrophilic functional group include a hydroxyl group, a carboxyl group, and a sulfonic acid group. Among these macrocyclic compounds, for example, calixarenes and cyclodextrin are particularly preferred.

The calixarene is a cyclic oligomer which has a phenol skeleton and which is formed through polymerizing 3 to 20 phenol molecules, preferably 4 to 8 phenol molecules, via methylene groups to a cyclic structure. No particular limitation is imposed on the calixarene, and a variety of calixarenes may be employed. Examples of the calixarene include calix(4)arene, calix(6)arene, calix(8)arene, calix(4)arenesulfonic acid, calix(6)arenesulfonic acid, calix(8)arenesulfonic acid, calix(4)areneacetic acid, calix(6)areneacetic acid, calix(8)areneacetic acid, calix(4)arenecarboxylic acid, calix(6)arenecarboxylic acid, calix(8)arenecarboxylic acid, calix(4)areneamine, calix(6)areneamine, calix(8)areneamine, and salts thereof. Among them, calix(6)arenesulfonic acid, calix(8)arenesulfonic acid, and salts thereof are preferred. Notably, "calix[6]arene-p-sulfonic acid, hexasodium salt, hydrate," or "calix[8]arene-p-sulfonic acid, octasodium salt, hydrate" may be commercially available from Dojindo Laboratories and are preferably employed from the viewpoint of availability. Alternatively, resorcinarenes having a resorcinol skeleton, pyrogallolarenes having a pyrogallol skeleton, calixpyrroles having a pyrrole skeleton, etc. may be employed. These calixarenes may be used in combination of two or more species. In use, the final calixarene concentration of the reaction system is preferably adjusted to 0.005 to 4 mM, more preferably to 0.005 to 3 mM, still more preferably to 0.005 to 2.5 mM, particularly preferably to 0.01 to 2 mM.

Cyclodextrin is a type of cyclic oligosaccharide having a cyclic structure which is formed through linking several D-glucose molecules via α(1→4) glucoside bonds. Cyclodextrins in which five or more glucose molecules are linked are known. Generally, cyclodextrins in which 6 to 8 glucose molecules are linked are used. A cyclodextrin in which six glucose molecules are linked is called α-cyclodextrin (cyclohexaamylose), a cyclodextrin in which seven glucose molecules are linked is called β-cyclodextrin (cycloheptaamylose), and a cyclodextrin in which eight glucose molecules are linked is called γ-cyclodextrin (cyclooctaamylose). However, the cyclodextrin is not particularly limited to these cyclodextrin species. For example, modified forms of these dextrins may also be employed. Specifically, a cyclodextrin modified form in which a hydrogen atom of a hydroxyl group of the cyclodextrin has been substituted by a certain functional group or a salt thereof may be used. Examples of such a modified cyclodextrin include alkyl-group-substituted alkylated cyclodextrin, acyl-group-substituted acylated cyclodextrin, carboxyalkyl-group-substituted carboxyalkylated cyclodextrin, hydroxyalkyl-group-substituted hydroxyalkylated cyclodextrin, sulfoalkyl-group-substituted sulfoalkylated cyclodextrin, and salts thereof. Alternatively, a cyclodextrin derivative in which a hydroxyl group of the cyclodextrin has been reacted with an acid to form an ester bond, or a salt thereof may be used. Examples of such a cyclodextrin derivative include cyclodextrin sulfonic acid ester or a salt thereof (Na salt: also called cyclodextrin sulfate) and cyclodextrin phosphoric acid ester or a salt thereof. Yet alternatively, there may also be employed a branched cyclodextrin in which a 6-position hydroxyl group of a glucose molecule forming the cyclodextrin has undergone dehydration condensation with a hydroxyl group of a saccharide such as glucose or maltose.

Among these cyclodextrins, β-cyclodextrin is preferably employed.

The cyclodextrin concentration of the reaction system is preferably 1 to 400 mM, particularly preferably 1 to 100 mM.

Among the aforementioned macrocyclic compounds, a calixarene is preferably employed as a main ingredient. Particularly when the macrocyclic compound is employed as a measurement sensitivity-enhancing agent, the final calixarene concentration of the reaction system is preferably adjusted to 0.005 to 4 mM, more preferably to 0.005 to 3 mM, particularly to 0.005 to 2.5 mM. When the macrocyclic compound is employed as a hemoglobin influence avoiding agent, the final calixarene concentration of the reaction system is preferably adjusted to 0.005 to 3 mM, more preferably to 0.01 to 2 mM.

If needed, conventional additives such as polyethylene glycol, dextran, gelatin, sodium chloride, and EDTA may be added to the reaction system.

So long as the macrocyclic compound is present in the antigen-antibody reaction system, the macrocyclic compound may be added to the sample before antigen-antibody reaction, or to a reagent containing an immunoreactive substance. Alternatively, the macrocyclic compound may also be added to a buffer employed in the reaction.

Absorbance may be measured through either the end-point method or the rate assay method. In the method of the present invention, the absorbance measuring method is not limited to the above methods, and may be modified in accordance with the immunoassay method employed. The buffer, measurement conditions, etc. employed in the present invention may also be appropriately modified.

The reagent of the present invention is a reagent employed in the aforementioned methods, and contains a measurement sensitivity enhancing agent or a hemoglobin influence avoiding agent containing the aforementioned macrocyclic compound as a main ingredient. The reagent may be appropriately prepared in accordance with the mode of the immunoassay method. The reagent may be a kit containing a plurality of component reagents. In this kit, at least one component reagent contains the aforementioned macrocyclic compound.

The range of pH used in the immunoassay method of the present invention is 4.5 to 9.5, preferably 5.5 to 8.5. In order to maintain the pH, an appropriate buffer is preferably used. Examples the buffer include phosphate buffer, Tris-HCl buffer, succinate buffer, glycine buffer, and Good's buffers; i.e., glycylglycine, MES (2-(N-morpholino)ethanesulfonic acid), HEPES (N-2-hydroxyethyl-piperazine-N'-ethanesulfonic acid), TES (N-tris(hydroxymethyl)methyl-2-aminoethanesulfonic acid), MOPS (3-(N-morpholino)propanesulfonic acid), PIPES (piperazine-1,4-bis(2-ethanesulfonic acid)), DIPSO (3-(N',N-bis(2-hydroxyethyl)amino)-2-hydroxypropanesulfonic acid), Tricine (tris(hydroxymethyl)methylglycine), TAPS(N-tris(hydroxymethyl)methyl-3-aminopropanesulfonic acid), etc. The buffer concentration is 1 to 500 mM, preferably 3 to 300 mM.

The immunoreaction mixture of the present invention may contain sodium azide, animal serum, γ-globulin, an antibody specific to human IgG or IgM, albumin, inorganic salts including sodium chloride, saccharides, amino acids, a chelating agent such as EDTA, an SH reagent such as DTT, or a surfactant. The sodium azide concentration is 0.01 to 1%, preferably 0.03 to 0.3%. The animal serum, γ-globulin, specific antibody, or albumin employed in the invention may be derived from a bovine, a horse, a pig, a sheep, a rabbit, a human, a rat, etc. These material may be modified forms or degradation products. These material may be added at appropriate concentrations. When sodium chloride is employed, the concentration is preferably about a physiological saline level. Other substances may be employed at appropriate concentrations.

EXAMPLES

The present invention will next be described in more detail by way of examples, which should not be construed as limiting the invention thereto.

Example 1

Assay of Soluble Fibrin (SF)

(1) Preparation of First Reagent

"Calix[8]arene p-sulfonic acid, octasodium salt, hydrate" or "calix[6]arene p-sulfonic acid, hexasodium salt, hydrate" (product of Dojindo Laboratories) was added to 30 mM Tris-HCl buffer (pH 8.5) containing 0.4% bovine serum albumin and 0.5M sodium chloride so that the calixarene concentration was adjusted to 0.01 to 10 mM (0.005 to 5 mM as final concentration of each reaction system), whereby first reagents were prepared. As a comparative example, a first reagent containing no calixarene was employed.

(2) Preparation of Second Reagent (Suspension of Anti-Soluble Fibrin (SF) Antibody-Immobilized Particles)

An anti-SF monoclonal antibody was diluted with 20 mM Tris-HCl buffer (pH 7.5) to a concentration of 0.7 mg/mL, to thereby prepare an antibody solution. The antibody solution was admixed with an equiamount of 1% suspension of polystyrene latex (product of Sekisui Medical, mean particle size: 0.2 µm), and the mixture was stirred at 4° C. for two hours. To the mixture, 1% bovine serum albumin was added, and the resultant mixture was stirred for one hour, and then centrifugation was performed. The precipitates were recovered and suspended in 5 mM MOPS (pH 7) containing 0.5% bovine serum albumin, to thereby prepare a second reagent (suspension of anti-SF antibody-immobilized particles).

(3) Samples

Purified fibrinogen was digested by thrombin, to thereby prepare acid-soluble desAABB fibrin. The fibrin was added to human citrate plasma so that the final fibrin concentration was adjusted to 10.3 µg/mL, to thereby prepare soluble fibrin samples. Note that physiological saline was used as a blank.

(4) Measurement

Each first reagent (100 µL) was added to each sample (3 µL), and the mixture was incubated at 37° C. for five minutes. Then, the second reagent (100 µL) was added thereto, and the mixture was stirred. The change in absorbance at 570 nm (main absorption wavelength) and 800 nm (sub absorption wavelength) from at 1 minute to 5 minute was measured. The results are shown in Tables 1 and 2.

As is clear from Tables 1 and 2, when a calixarene was added to a reaction mixture at a final concentration of 5 mM, anomalous blank values were obtained, failing to obtain accurate assay values. However, within a calixarene final concentration range of 0.005 to 4 mM (reaction system), the SF measurement sensitivity was found to increase.

Example 2

Assay of Soluble Fibrin (SF)

In a manner similar to Example 1, acid-soluble desAABB fibrin was added to human citric acid plasma so that the final fibrin concentration was adjusted to 10.3 µg/mL and 20.1 µg/mL, to thereby prepare soluble fibrin samples. First reagents having a final calixarene concentration of 0.005 to 2 mM were employed in the assay. The same second reagent as employed in Example 1 was used. In Comparative Example, a first reagent containing no calixarene was used. Tables 3 and 4 show the relation between absorbance and SF concentration.

TABLE 1

| Additive | Comp. Ex. | Calix[8]arene p-sulfonic acid, octasodium salt, hydrate | | | | | | | | | |
|---|---|---|---|---|---|---|---|---|---|---|---|
| Concentration (1st reagent) | — | 10 mM | 8 mM | 6 mM | 4 mM | 2 mM | 1 mM | 0.2 mM | 0.1 mM | 0.02 mM | 0.01 mM |
| Concentration (reaction mixture) | — | 5 mM | 4 mM | 3 mM | 2 mM | 1 mM | 0.5 mM | 0.1 mM | 0.05 mM | 0.01 mM | 0.005 mM |
| Blank | −3.8 | 198.9 | 8.1 | −5.7 | −4.9 | −5.9 | −3.7 | −4.2 | −6.0 | −2.8 | −4.0 |
| SF concentration 0.0 µg/mL | 0.0 | 0.0 | 0.0 | 0.0 | 0.0 | 0.0 | 0.0 | 0.0 | 0.0 | 0.0 | 0.0 |
| SF concentration 10.3 µg/mL | 28.4 | 24.7 | 301.7 | 392.0 | 156.1 | 89.0 | 72.8 | 89.3 | 80.2 | 36.1 | 33.3 |

(mAbs)

TABLE 2

| Additive | Comp. Ex. | Calix[6]arene p-sulfonic acid, hexasodium salt, hydrate | | | | | | | | | |
|---|---|---|---|---|---|---|---|---|---|---|---|
| Concentration (1st reagent) | — | 10 mM | 8 mM | 6 mM | 4 mM | 2 mM | 1 mM | 0.2 mM | 0.1 mM | 0.02 mM | 0.01 mM |
| Concentration (reaction mixture) | — | 5 mM | 4 mM | 3 mM | 2 mM | 1 mM | 0.5 mM | 0.1 mM | 0.05 mM | 0.01 mM | 0.005 mM |
| Blank | −3.8 | 377.3 | 1.5 | −4.5 | −9.4 | −4.5 | −5.1 | −6.2 | −4.0 | −7.3 | −4.3 |
| SF concentration 0.0 µg/mL | 0.0 | 0.0 | 0.0 | 0.0 | 0.0 | 0.0 | 0.0 | 0.0 | 0.0 | 0.0 | 0.0 |
| SF concentration 10.3 µg/mL | 28.4 | −145.4 | 379.5 | 311.6 | 155.6 | 100.1 | 92.0 | 68.3 | 63.3 | 45.6 | 32.0 |

(mAbs)

TABLE 3

| Additive | Comp. Ex. | Calix[8]arene p-sulfonic acid, octasodium salt, hydrate | | | | | | | |
|---|---|---|---|---|---|---|---|---|---|
| Concentration (1st reagent) | — | 10 mM | 4 mM | 2 mM | 1 mM | 0.2 mM | 0.1 mM | 0.02 mM | 0.01 mM |
| Concentration (reaction mixture) | — | 5 mM | 2 mM | 1 mM | 0.5 mM | 0.1 mM | 0.05 mM | 0.01 mM | 0.005 mM |
| SF concentration 0.0 µg/mL | 0.0 | 0.0 | 0.0 | 0.0 | 0.0 | 0.0 | 0.0 | 0.0 | 0.0 |
| SF concentration 10.3 µg/mL | 28.4 | 24.7 | 156.1 | 89.0 | 72.8 | 89.3 | 80.2 | 36.1 | 33.3 |
| SF concentration 20.1 µg/mL | 56.4 | 25.7 | 160.0 | 101.4 | 84.9 | 106.7 | 103.2 | 63.0 | 62.2 |

(mAbs)

TABLE 4

| Additive | Comp. Ex. | Calix[6]arene p-sulfonic acid, hexasodium salt, hydrate | | | | | | | |
|---|---|---|---|---|---|---|---|---|---|
| Concentration (1st reagent) | — | 10 mM | 4 mM | 2 mM | 1 mM | 0.2 mM | 0.1 mM | 0.02 mM | 0.01 mM |
| Concentration (reaction mixture) | — | 5 mM | 2 mM | 1 mM | 0.5 mM | 0.1 mM | 0.05 mM | 0.01 mM | 0.005 mM |
| SF concentration 0.0 µg/mL | 0.0 | 0.0 | 0.0 | 0.0 | 0.0 | 0.0 | 0.0 | 0.0 | 0.0 |
| SF concentration 10.3 µg/mL | 28.4 | −145.4 | 155.6 | 100.1 | 92.0 | 68.3 | 63.3 | 45.6 | 32.0 |
| SF concentration 20.1 µg/mL | 56.4 | −145.0 | 168.9 | 115.8 | 101.9 | 89.5 | 87.0 | 71.4 | 64.6 |

(mAbs)

As is clear from Tables 3 and 4, when a calixarene was added to a reaction mixture at a final concentration falling within a range of 0.005 to 2 mM, the SF measurement sensitivity was found to increase, as compared with Comparative Example in which no calixarene was used. The reaction was found to be antigen-concentration-dependent. The assaying method of the invention is particularly useful in a sample having a low target substance concentration.

Example 3

Assay of Lipoprotein (a) (Lp(a))

(1) Preparation of First Reagents

"Calix[8]arene p-sulfonic acid, octasodium salt, hydrate" or "calix[6]arene p-sulfonic acid, hexasodium salt, hydrate" (product of Dojindo Laboratories) was admixed with 0.05M glycine buffer (pH 9) containing 0.2M sodium chloride so that the calixarene concentration was adjusted to 0.01 to 5 mM (0.005 to 2.5 mM as final concentration of each reaction system), whereby first reagents were prepared. As a comparative example, a first reagent containing no calixarene was employed.

(2) Preparation of a Second Reagent (Suspension of Anti-Lp (a) Antibody-Immobilized Particles)

A monoclonal antibody which causes immuno-agglutination with a single use obtained from mice through a routine method employing purified human apo(a) serving as an immunogen was admixed with 0.05M glycine buffer (pH 9) to an antibody concentration of 1.4 mg/mL, to thereby prepare an antibody solution. The monoclonal antibody is produced by a hybridoma 28205 (FERM BP-3755) deposited in National Institute of Advanced Industrial Science and Technology (hereinafter the monoclonal antibody is referred to as "anti-Lp(a) monoclonal antibody." This antibody solution was added to an equiamount of 5% suspension of polystyrene latex (product of Sekisui Medical, mean particle size: 0.1 µm), and the mixture was stirred at 4° C. for two hours. The resultant mixture was centrifuged to thereby remove the supernatant, and 0.05M glycine buffer (pH 9) containing 2% bovine serum albumin was added to the thus-recovered precipitates. The obtained mixture was stirred overnight at 4° C. and then centrifuged. The thus-collected precipitates suspended in 0.05M glycine buffer (pH 9) containing 2% bovine serum albumin, to thereby prepare a suspension of anti-Lp(a) antibody-immobilized particles).

(3) Samples

Serum whose Lp(a) concentrations were each known were employed.

(4) Assay of Lp(a)

Each first reagent (100 µL) was added to each Lp(a)-containing sample (2.5 µL), and the mixture was incubated at 37° C. for five minutes. Then, the second reagent (100 µL) was added thereto, and the mixture was stirred. The change in absorbance at 570 nm (main absorption wavelength) and 800 nm (sub absorption wavelength) from at 1 minute to 5 minute was measured. The relationship between obtained absorbance and Lp(a) concentration are shown in Tables 5 and 6.

TABLE 5

| Additive | Comp. Ex. | Calix[8]arene p-sulfonic acid, octasodium salt, hydrate | | | | | | |
|---|---|---|---|---|---|---|---|---|
| Concentration (1st reagent) | — | 5 mM | 4 mM | 3 mM | 2 mM | 1 mM | 0.1 mM | 0.01 mM |
| Concentration (reaction mixture) | — | 2.5 mM | 2 mM | 1.5 mM | 1 mM | 0.5 mM | 0.05 mM | 0.005 mM |
| Physiological saline | 0.0 | 0.0 | 0.0 | 0.0 | 0.0 | 0.0 | 0.0 | 0.0 |
| Lp(a) concentration 17.5 mg/dL | 38.8 | 44.7 | 45.1 | 45.2 | 44.9 | 42.7 | 43.0 | 39.1 |
| Lp(a) concentration 47.1 mg/dL | 140.2 | 159.0 | 161.8 | 161.1 | 163.0 | 160.5 | 156.7 | 142.9 |
| Lp(a) concentration 112.5 mg/dL | 302.4 | 369.8 | 368.8 | 368.9 | 369.2 | 358.0 | 342.6 | 311.4 |

(mAbs)

TABLE 6

| Additive | Comp. Ex. | Calix[6]arene p-sulfonic acid, hexasodium salt, hydrate | | | | | | |
|---|---|---|---|---|---|---|---|---|
| Concentration (1st reagent) | — | 5 mM | 4 mM | 3 mM | 2 mM | 1 mM | 0.1 mM | 0.01 mM |
| Concentration (reaction mixture) | — | 2.5 mM | 2 mM | 1.5 mM | 1 mM | 0.5 mM | 0.05 mM | 0.005 mM |
| Physiological saline | 0.0 | 0.0 | 0.0 | 0.0 | 0.0 | 0.0 | 0.0 | 0.0 |
| Lp(a) concentration 17.5 mg/dL | 38.8 | 48.0 | 47.2 | 48.0 | 48.2 | 47.6 | 43.5 | 39.9 |
| Lp(a) concentration 47.1 mg/dL | 140.2 | 172.1 | 170.8 | 172.0 | 173.5 | 174.1 | 157.6 | 144.5 |
| Lp(a) concentration 112.5 mg/dL | 302.4 | 408.3 | 409.5 | 414.7 | 421.6 | 406.0 | 342.0 | 318.0 |

(mAbs)

As is clear from Tables 5 and 6, when a calixarene was added to a reaction mixture at a final concentration falling within a range of 0.005 to 2.5 mM, the Lp(a) measurement sensitivity was found to increase.

Example 4

Assay of Soluble Fibrin (SF))

(1) Preparation of First Reagents

"Calix[6]arene p-sulfonic acid, hexasodium salt, hydrate" (product of Dojindo Laboratories) was added to 30 mM Tris-HCl buffer (pH 8.5) containing 0.4% bovine serum albumin and 0.5M sodium chloride so that the calixarene concentration was adjusted to 0.01 to 6 mM (0.005 to 3 mM as final concentration of each reaction system), whereby first reagents were prepared. As a comparative example, a first reagent containing no calixarene was employed.

(2) Preparation of a Second Reagent (Suspension of Anti-Soluble Fibrin (SF) Antibody-Immobilized Particles)

An anti-SF monoclonal antibody was diluted with 20 mM Tris-HCl buffer (pH 7.5) to a concentration of 0.7 mg/mL, to thereby prepare an antibody solution. The antibody solution was admixed with an equiamount of 1% suspension of polystyrene latex (product of Sekisui Medical, mean particle size: 0.2 μm), and the mixture was stirred at 4° C. for two hours. To the mixture, 1% bovine serum albumin was added, and the resultant mixture was stirred for one hour, and then centrifugation was performed. The precipitates were recovered and suspended in 5 mM MOPS (pH 7) containing 0.5% bovine serum albumin, to thereby prepare a second reagent (suspension of anti-SF antibody-immobilized particles).

(3) Samples

Hemolytic hemoglobin samples were prepared with interference check A plus (Sysmex CORPORATION) so that the hemoglobin concentration was adjusted to 0 to 500 mg/dL.

(4) Assay

Each first reagent (100 μL) was added to each sample (3 μL), and the mixture was incubated at 37° C. for five minutes. Then, the second reagent (100 μL) was added thereto, and the mixture was stirred. The change in absorbance at 570 nm (main absorption wavelength) and 800 nm (sub absorption wavelength) from at 1 minute to 5 min was measured. The results of absorbance measurements are shown in Table 7.

TABLE 7

| Additive | Comp. Ex. | Calix[6]arene p-sulfonic acid, hexasodium salt, hydrate | | | | | | |
|---|---|---|---|---|---|---|---|---|
| Concentration (1st reagent) | — | 6 mM | 4 mM | 2 mM | 1 mM | 0.2 mM | 0.1 mM | 0.02 mM | 0.01 mM |
| Concentration (reaction mixture) | — | 3 mM | 2 mM | 1 mM | 0.5 mM | 0.1 mM | 0.05 mM | 0.01 mM | 0.005 mM |
| hemoglobin 0 mg/dL | 0.8 | −1.5 | 1.9 | −1.0 | −3.1 | −3.0 | −3.9 | 3.4 | 0.6 |
| hemoglobin 100 mg/dL | 2.8 | −0.6 | 4.8 | −4.7 | −0.2 | 0.1 | −1.1 | 4.5 | 5.5 |
| hemoglobin 200 mg/dL | 6.8 | −2.5 | 5.0 | 1.4 | 1.3 | 3.9 | 1.6 | 11.7 | 9.9 |
| hemoglobin 300 mg/dL | 16.5 | 0.0 | 7.0 | −1.4 | 2.1 | 2.7 | 3.0 | 14.6 | 11.8 |
| hemoglobin 400 mg/dL | 25.8 | 4.6 | 5.9 | −2.4 | 1.3 | 5.7 | 6.0 | 20.2 | 19.3 |
| hemoglobin 500 mg/dL | 32.0 | 0.7 | 1.5 | 2.8 | 1.8 | 6.0 | 10.5 | 26.0 | 27.8 |

(mAbs)

As is clear from Table 7, when a calix(6)arene was added as a macrocyclic compound to a reaction mixture at a final concentration falling within a range of 0.005 to 3 mM, the influence of hemoglobin on absorbance measurements was found to be suppressed.

Example 5

Assay of Soluble Fibrin (SF)

The assaying procedure in Example 4 was repeated, except that "calix[8]arene p-sulfonic acid, octasodium salt, hydrate" (product of Dojindo Laboratories) was used instead of "calix[6]arene p-sulfonic acid, hexasodium salt, hydrate," at a calixarene concentration of the first reagent of 0.01 to 4 mM (0.005 to 2 mM as final concentration of each reaction system). Table 8 shows the results of absorbance measurements.

TABLE 8

| Additive | Comp. Ex. | Calix[8]arene p-sulfonic acid, octasodium salt, hydrate | | | | | | |
|---|---|---|---|---|---|---|---|---|
| Concentration (1st reagent) | — | 4 mM | 2 mM | 1 mM | 0.2 mM | 0.1 mM | 0.02 mM | 0.01 mM |
| Concentration (reaction mixture) | — | 2 mM | 1 mM | 0.5 mM | 0.1 mM | 0.05 mM | 0.01 mM | 0.005 mM |
| hemoglobin 0 mg/dL | 0.8 | 0.5 | 2.4 | −1.7 | −3.2 | −1.3 | 0.2 | 0.1 |
| hemoglobin 100 mg/dL | 2.8 | 0.5 | 1.8 | −1.9 | −0.1 | 0.1 | 2.3 | 5.8 |
| hemoglobin 200 mg/dL | 6.8 | 1.1 | 1.3 | −0.8 | 0.4 | 2.5 | 2.2 | 6.5 |
| hemoglobin 300 mg/dL | 16.5 | 3.8 | 2.3 | −3.6 | −0.7 | −0.5 | 5.4 | 10.1 |
| hemoglobin 400 mg/dL | 25.8 | 7.4 | 0.5 | 0.3 | 1.5 | −1.7 | 8.8 | 18.4 |
| hemoglobin 500 mg/dL | 32.0 | 10.6 | 8.1 | 0.5 | 1.0 | 2.6 | 12.7 | 23.8 |

(mAbs)

As is clear from Table 8, when a calix(8)arene was added as a macrocyclic compound to a reaction mixture at a final concentration falling within a range of 0.005 to 2 mM, the influence of hemoglobin on absorbance measurements was found to be suppressed.

Example 6

Assay of Soluble Fibrin (SF)

The assaying procedure in Example 4 was repeated, except that β-cyclodextrin was used instead of calix[6]arene p-sulfonic acid, hexasodium salt, hydrate, at a calixarene concentration of 10 mM or 40 mM (5 or 20 mM as final concentration of each reaction system). Table 9 shows the results of absorbance measurements.

TABLE 9

| Additive | Comp. Ex. | β-cyclodextrin | sulfated |
|---|---|---|---|
| Concentration (1st reagent) | — | 40 mM | 10 mM |
| Concentration (reaction mixture) | — | 20 mM | 5 mM |
| hemoglobin 0 mg/dL | 0.8 | 2.9 | 1.0 |
| hemoglobin 100 mg/dL | 2.8 | 4.2 | 3.5 |
| hemoglobin 200 mg/dL | 6.8 | 3.3 | 4.6 |
| hemoglobin 300 mg/dL | 16.5 | 6.7 | 9.6 |
| hemoglobin 400 mg/dL | 25.8 | 8.3 | 15.9 |
| hemoglobin 500 mg/dL | 32.0 | 9.1 | 20.7 |

(mAbs)

As is clear from Table 9, when β-cyclodextrin was added as a macrocyclic compound to a reaction mixture at a final concentration falling within a range of 5 to 20 mM, the influence of hemoglobin on absorbance measurements was found to be suppressed.

The invention claimed is:

1. A method for enhancing measurement sensitivity or avoiding hemoglobin influence in a latex agglutination or metal agglutination immunoassay method, the method comprising:
   performing a latex agglutination or metal agglutination immunoassay of a biological sample comprising a target antigen and hemoglobin with an antibody sensitized insoluble carrier in the presence of calixarene at a final concentration of 0.005 to 4 mM.

2. The method according to claim 1, wherein the method is for enhancing measurement sensitivity.

3. The method according to claim 1, wherein the method is a hemoglobin influence avoiding method.

4. The method according to claim 1, wherein the insoluble carrier comprises latex particles or metal colloid particles.

5. The method according to claim 4, wherein the insoluble carrier comprises latex particles.

6. The method according to claim 4, wherein the insoluble carrier comprises metal colloid particles.

7. The method according to claim 1, wherein the target antigen is a protein antigen.

8. The method according to claim 1, wherein the hemoglobin concentration in the biological sample is adjusted to from 0 to 500 mg/dL.

* * * * *